(12) United States Patent
Soffiatti et al.

(10) Patent No.: US 10,905,794 B2
(45) Date of Patent: *Feb. 2, 2021

(54) PLASTIC MATERIAL FOR DEVICES TO BE IMPLANTED INTO THE HUMAN BODY OR FOR ARTICULAR SPACERS

(71) Applicant: TECRES S.p.A., Sommacampagna (IT)

(72) Inventors: Renzo Soffiatti, Nogara (IT); Giovanni Faccioli, Monzambano (IT)

(73) Assignee: TECRES S.P.A., Sommacampagna (IT)

( * ) Notice: Subject to any disclaimer, the term of this patent is extended or adjusted under 35 U.S.C. 154(b) by 150 days.

This patent is subject to a terminal disclaimer.

(21) Appl. No.: 15/549,808

(22) PCT Filed: Feb. 16, 2016

(86) PCT No.: PCT/IB2016/050818
§ 371 (c)(1),
(2) Date: Aug. 9, 2017

(87) PCT Pub. No.: WO2016/132288
PCT Pub. Date: Aug. 25, 2016

(65) Prior Publication Data
US 2018/0028717 A1    Feb. 1, 2018

(30) Foreign Application Priority Data
Feb. 16, 2015    (IT) .......................... ITVR2015A0021

(51) Int. Cl.
| | | |
|---|---|---|
| A61L 27/16 | (2006.01) | |
| A61L 27/54 | (2006.01) | |
| A61L 27/18 | (2006.01) | |
| A61L 27/46 | (2006.01) | |
| A61L 27/56 | (2006.01) | |
| B29B 7/00 | (2006.01) | |
| B29B 9/02 | (2006.01) | |
| B29K 23/00 | (2006.01) | |
| B29K 105/00 | (2006.01) | |

(52) U.S. Cl.
CPC ............... *A61L 27/16* (2013.01); *A61L 27/18* (2013.01); *A61L 27/46* (2013.01); *A61L 27/54* (2013.01); *A61L 27/56* (2013.01); *A61L 2300/404* (2013.01); *A61L 2300/406* (2013.01); *A61L 2300/44* (2013.01); *A61L 2300/45* (2013.01); *A61L 2400/06* (2013.01); *A61L 2430/02* (2013.01); *A61L 2430/24* (2013.01); *B29B 7/005* (2013.01); *B29B 9/02* (2013.01); *B29K 2023/0683* (2013.01); *B29K 2105/0035* (2013.01)

(58) Field of Classification Search
CPC .......... A61L 27/16; A61L 27/56; A61L 27/54; A61L 27/46; A61L 27/18; A61L 2300/45; A61L 2300/406; A61L 2300/44; A61L 2400/06; A61L 2430/02; A61L 2430/24; A61L 2300/404; B29K 2023/0683; B29K 2105/0035; B29B 7/005; B29B 9/02
See application file for complete search history.

(56) References Cited

U.S. PATENT DOCUMENTS

| | | | |
|---|---|---|---|
| 6,641,831 B1 | 11/2003 | Schierholz | |
| 2005/0065307 A1* | 3/2005 | King | A61L 27/56 526/352 |
| 2011/0125265 A1* | 5/2011 | Bagga | A61B 17/68 623/16.11 |
| 2011/0306698 A1* | 12/2011 | Pletcher | C08K 5/005 522/161 |
| 2013/0171410 A1* | 7/2013 | Armbruster | A61B 17/70 428/132 |

FOREIGN PATENT DOCUMENTS

| | | | |
|---|---|---|---|
| CN | 101791407 | * | 8/2010 |
| DE | 102007052519 | | 4/2009 |
| WO | 2010096053 | | 8/2010 |
| WO | 2013184010 | | 12/2013 |

OTHER PUBLICATIONS

International Search Report dated May 17, 2016 for PCT/IB2016/050818 (3 pages).
International Preliminary Search Report dated May 17, 2017 for PCT/IB2016/050818 (10 pages).

* cited by examiner

*Primary Examiner* — Robert S Cabral
(74) *Attorney, Agent, or Firm* — Tutunjian & Bitetto, P.C.

(57) ABSTRACT

Biocompatible and implantable in the human body plastic material, for the obtainment of a device that can be implanted in the human body or a spacer device in order to treat a bone or a joint location, including an acrylic resin or polyethylene (PE) or low density polyethylene or high density polyethylene or ultra-high molecular weight polyethylene (UHMWPE) or polypropylene or polyamide or polyetheretherketone (PEEK) or a thermosetting resin or a mixture of the same, wherein the material can be molded and includes at least one pharmaceutical or medical substance; device implantable in the human body or spacer device for treating a bone or a joint location, obtained by the material above and method for manufacturing the material according to the present invention.

14 Claims, No Drawings

PLASTIC MATERIAL FOR DEVICES TO BE IMPLANTED INTO THE HUMAN BODY OR FOR ARTICULAR SPACERS

TECHNICAL FIELD OF THE INVENTION

The present invention relates to an antibiotic-loaded plastic material to be used for the molding or production of devices to be implanted in the human body.

In particular, according to one version of the invention, such antibiotic-loaded material is polyethylene.

STATE OF THE ART

Polyethene, or more commonly known as polyethylene is the simplest of synthetic polymers and the most common among plastic materials.

It is often addressed with the abbreviation "PE", and its chemical formula is $(-C_2H_4-)_n$ where n can reach several millions.

PE polymeric chains can have variable length and can be more or less branched.

Polyethylene is a thermoplastic resin, with excellent insulating and chemical stability properties; further, it is a very versatile material and is one of the most cost-effective plastic material.

Types of material having different properties and applications are obtained based on the PE molecular weights distribution and entity of branching. For example, ultra-high molecular weight polyethylene (UHMWPE) is a polyethylene with average molecular weight between $3 \times 10^6$ and $6 \times 10^6$ u (according to the standard ASTM D4020). A material with well packed chains in the crystalline structure and very resistant results.

This type of polyethylene is usually synthesized through metallocene coordination polymerization.

Unlike other more common types of PE, its particular mechanical properties make it suitable for specific applications, such as medical prosthesis.

There is, also, high density polyethylene (HDPE) or (PEAD), which is not branched and thus presents high intermolecular forces and higher rigidity than low density polyethylene; low density polyethylene (LDPE), which is more branched than HDPE and is, therefore, a more ductile and less rigid material; low density linear polyethylene (LLDPE), which is substantially a linear PE having a significant number of short branches.

UHMWPE shows long chains which make the material very tough and resistant, with the highest resistance to impacts, with respect to the other thermoplastic materials.

UHMWPE has a very low ability to absorb liquids or humidity; moreover, it has an extremely low friction coefficient and for this it is considered a self-lubricating material.

It shows also a high resistance to abrasion.

These characteristics make UHMWPE an extremely versatile material, to be widely used also in medical area, for example for the production of devices implantable in the human body or spacer devices, designed for treating a bone or articular seat, there where the mechanical and tribological performances are of primary importance.

Anyway, other types of polyethylene are also usable in medical field, for example for the production of devices implantable in the human body or spacer devices, designed for treating a bone or joint location.

Other plastic materials can have excellent mechanical or physical characteristics, useful for the medical or orthopedic field.

Accordingly, the need of a biocompatible and implantable plastic material is felt, loaded or loadable with pharmaceutical or medical substances, such as at least one antibiotic, to be used for molding or manufacturing devices implantable in the human body or spacer devices.

SUMMARY OF THE INVENTION

The task of the present invention is that of improving the prior art.

Within such task, it is an object of the present invention to provide for a biocompatible and implantable plastic material, comprising a pharmaceutical or medical substance.

One object of the present invention is to provide for a biocompatible and implantable material which is suitable for being used in the molding technique and/or for being extrudable.

In compliance to one aspect of the present invention, a biocompatible and implantable plastic material is provided according to the present application.

In accordance with another aspect of the present invention, a device to be implanted in the human body or a spacer device is provided, for treatment of a bone or articular seat, (the device being) made of a biocompatible and implantable plastic material, according to the present application.

One advantage of such a device to be implanted in the human body or spacer device for treatment of a bone or joint location is that of containing pharmaceutical or medical substances, such as at least one antibiotic, and at the same time, having a low friction coefficient.

Another advantage of such a device to be implanted in the human body or a spacer device for treating a bone or joint location consists in the fact of containing pharmaceutical or medical substances, such as one antibiotic, and the same time, having excellent resistance and/or toughness properties.

A further advantage of the device to be implanted in the human body or of a spacer device for treating a bone or articular seat is that it is self-lubricating.

Moreover, being it moldable, such device can be customized or manufactured in series in an easy and fast way, substantially without the need of further surface finishing.

According to another aspect of the present invention, a method for the manufacturing of a biocompatible and implantable plastic material is provided, which material contains a pharmaceutical or medical substance, such as an antibiotic, and is suitable for being used in one molding technique, according to the present application.

One advantage of such method is that of being simple and fast, substantially without the need of further steps of surface finishing.

The present application refers to preferred and advantageous embodiments of the invention.

DETAILED DESCRIPTION OF THE INVENTION

The present invention relates to a plastic material biocompatible and implantable in the human body, for the manufacturing of an implantable device in the human body or of a spacer device for treating a bone or joint location.

Such plastic material, which comprises a pharmaceutical or medical substance, can comprise one or more of the following materials; an acrylic resin or polyethylene (PE) or low density polyethylene or high density polyethylene or ultra-high molecular weight polyethylene (UHMWPE) or polypropylene or polyamide or polyetheretherketone (PEEK) or a mixture of the same.

Thermoplastic resins (such PE, PMMA, PP, PS, ABS, PEEK, PA, etc., at least some of them form object of the present invention), as it is known, melt through heating. In other words, a product, i.e. an object molded with thermoplastic resins, if heated will soften first and then will melt. Each resin has its own melting or softening point. At the melting state they can be easily injected into a mold. Once they reach the mold, they cool and harden into the geometry given by the mold.

In one version of the invention, as will be clarified below, the pharmaceutical or medical substance can comprise or consist of gentamicin, in particular in one version Gentamicin Sulphate. Gentamicin sulphate is a crystalline solid at room temperature while, when it is heated at about 180° C., it melts because it has reached its melting point (PF). If the heating goes on, the temperature gets higher overcoming the PF and gentamicin becomes carbonized, irremediably losing its antibiotic virtues.

When a suitable resin is added to Gentamicin Sulphate, it is possible to heat it all at a temperature lower than 180° C. (for example gentamicin PF) and obtain a liquid melted mass which can be thrusted into a mold. Such thrust into the mold can be effortless.

In the case where the used resin is, for example, the PE—by heating at a temperature of about 170° C.—it is possible to obtain a sufficiently melted mass or mixture to be extruded with a normal press.

In a further version of the invention, the plastic material, comprising a pharmaceutical or medical substance, can comprise one or more of the following materials: one thermosetting resin, such as silicone, silicone elastomer, polyurethane, rigid and/or elastic polyurethane, other thermoplastic resins used, as the previous ones, in medical filed, etcetera.

Such resins, in one version of the invention, can be used as carrier for a pharmaceutical or medical substance, such as an antibiotic.

These thermosetting resins, once molded, can never be fused or liquefied through heating. The molding technique of such resins follows numerous procedures. For example, the silicone is prepared by transferring, in a mold, the mixture of two components: component A, which is the base resin, and component B, which instead is the hardening catalyst. At times it is necessary to heat the mixture to speed up the hardening.

Such plastic materials or thermosetting resins, in one version of the invention, are insoluble.

In a further version of the invention, the plastic material is soluble and comprises, for example, polylactic or polyglycolic acid polymers.

Between the acrylic resins it is possible to remember an acrylic copolymer made of MMA, styrene and ethyl-acrylate or the polymethyl methacrylate or mixtures comprising acrylic polymers and/or acrylic co-polymers.

In one specific version on the present invention, the material according to the present invention comprises ultra-high molecular weight polyethylene (UHMWPE) and one pharmaceutical or medical substance, such as at least one antibiotic.

The at least one pharmaceutical or medical substance, in one version of the invention, is uniformly distributed in the plastic material.

One of the main characteristics of such biocompatible material is that the same is moldable, for example by injection molding or thermo-injection or extrusion by means of molding presses or a thermoplastic molding technique or thermosetting molding.

Moreover, such plastic material, considering in particular UHMWPE, is self-lubricating because of its low friction coefficient.

Such characteristic is particularly advantageous for those devices that are implanted in areas undergoing rubbing or friction, such as one joint area. Such biocompatible material is moldable and, particularly when three-dimensional molding is regarded, it is possible to obtain through a simple and fast procedure medical devices or spacer devices containing a pharmaceutical or medical substance, both manufactured in series and customized.

In this latter case, in fact, it is possible to obtain a three-dimensional model of the device to produce, by selecting the dimensions and the shape or conformation more suitable for the surgical or anatomical needs of the patient, and manufacture the respective device suitable for the specific patient.

The pharmaceutical or medical substance comprised in the material according to the present invention can be made of at least one antibiotic, for example gentamicin sulphate or another suitable antibiotic, or an antiseptic agent of organic or inorganic nature, a bacteriostatic agent, such as silver in its many forms such as metallic powder or salts such as citrate, proteinate, colloidal, electrolytic, or other forms that can be used in the human body, or copper or gold in their forms or as salts, etcetera.

In one version of the invention, the pharmaceutical or medical substance is or comprises one organic antibiotic.

Such option is particularly relevant when the device obtainable with said material is a device to be implanted in the human body or a spacer device for the treatment of an infection in one bone or articular seat.

The function of the spacer devices, in fact, is just that of maintaining the joint space left by an infected prosthesis, which prosthesis is in fact removed for that reason, and at the same time that of treating the bone location infection, comprising in its inside for example a pharmaceutical or medical substance, such as at least one antibiotic, to be eluted in the treatment area.

Alternatively or in addition, the biocompatible material according to the present invention can also comprise one radio-opacifying agent, such as metallic powders for example tungsten, tantalum, silver or salts such as barium sulphate, zirconium oxide, bismuth oxide, etcetera.

Such agents, as it is known, are visible to X-rays and, therefore, they make it possible to monitor the position of the device to be implanted in the human body or the spacer device, as well as the material which contains such agents according to the present invention.

Moreover, the material according to the present invention can comprise further additives of medical kind, such as soluble and/or reabsorbable ceramic material, in the form of powder or granules, such as tricalcium phosphate or calcium sulphate or hydroxyapatite, or alumina in its various chemical forms, etcetera, or coloring substances of the biocompatible type and adapted to be introduced in the human body, etcetera.

Such additives, if not soluble or reabsorbable, can permanently stay within the human body, or be removed when the biocompatible and implantable plastic material in which they are contained is removed.

The biocompatible material according to the present invention, according to one version of the invention, is porous. Such porosity can be due to the fact of comprising at least one pharmaceutical or medical substance and, after its obtainment procedure, as it is better explained below.

One disadvantage of the plastic materials in general, or UHMWPE in particular, is that, due to the long polymeric chains, their molecules cannot slide easily one over the other without damaging or degrading.

For this reason, in some cases, the plastic materials have to be heated at temperatures close to their melting or vitreous transition temperatures, and thus at very high temperature, in order to be extruded or molded.

Accordingly, some possible pharmaceutical or medical substances therein contained, for example in particular antibiotic and more particularly organic antibiotic, in the case they have degradation temperatures lower than those of melting or vitreous transition of the plastic material, would be damaged by such heating, preventing de facto the material in object from being molded or extruded.

Conversely, it can occur that some plastic materials, such as UHMWPE, are not much resistant to high temperatures, having a melting point around 130-136 C. At higher temperatures, the material can easily degrade.

Thus, in the production of the material according to the present invention, temperature plays a fundamental role for maintaining the properties of the resulting material.

The plastic material according to the present invention, for example UHMWPE, is usually found in the form of rods or plates.

Such rods or plates are, accordingly, crushed or milled in order to obtain a granular pellet having dimensions of few millimeters or lower.

At least one pharmaceutical or medical substance, also in the form of powder or granules, is added to such granular pellet. In this way, solid-in-solid dispersion is obtained, made of the plastic material and the above mentioned at least one pharmaceutical or medical substance.

Such solid-in-solid dispersion is inserted in a specific apparatus, able to melt the materials therein contained, for example at about 130° C. According to a non-limiting example of the present invention, such apparatus comprises a loading hopper, an extrusion nozzle and a containing body, between the loading hopper and the nozzle, wherein the material passes, in case being blended. Such containing body presents continuous and adjacent areas at gradually growing temperature (up to a threshold value under which the dispersion does not degrade or does not lose its specific properties), in such a way the melting or softening of the material is obtained, preventing at the same time the degradation thereof.

For example, if the dispersion contains gentamicin sulphate, the same melts at about 184° C., thus, under that threshold (or better about 180° C.), it does not melt and keeps unchanged its antibiotic action.

In this case (or according to further versions of the invention), the biocompatible material is molded at a lower than 180° C. temperature, in order to avoid gentamicin degradation, or in general of the organic antibiotic, or more generally of the pharmaceutical or medical substance.

In this case, the extrusion line is very short, in the order of few millimeters, so as to overcome the poor sliding properties of the plastic material, when for example the UHMWPE is used.

In this way, it is possible to obtain implantable devices or spacer devices provided with at least one pharmaceutical or medical substance and made of the above mentioned plastic materials, which materials, not being incorporated with the bone tissue or the bone cements of traditional type, can be easily removed once their function has been carried out, or depending on the specific needs of the patient.

Moreover, when made of a plastic material having a low friction coefficient, such devices can be made substantially in a single piece, without having to produce ad hoc sliding surface, which surfaces, lacking pharmaceutical or medical substances, such as at least one antibiotics, could undergo an infection.

Moreover, composite devices made of more materials can be obtained, wherein some portions thereof, such as stems or screws or components in direct contact with the bone tissue—which must be able to be removed at a later time— are made of such material while other components are made with other materials, such as antibiotic-filled bone cement of the traditional type.

In the milling or blending step, if present, at least one radio-opacifying substance or a further additive of the ones described above is added.

Alternatively, the solid-in-solid dispersion is input in a mold, which mold is heated thereby obtaining the softening or a thermal sintering with consequent molding of the plastic material according to the present invention. Also in this case, the heating temperature is kept lower than a threshold value, thereby preventing the dispersion materials, such as the antibiotics or the organic antibiotics therein contained, from being degraded or losing their specific properties.

Such material, as said, can be molded by means of injection molding or thermo-injection or extrusion or by means of molding presses or by means of a thermoplastic or thermosetting molding technique, in order to obtain a device implantable in the human body or a spacer device for treating a bone or joint location.

By means of the material referred to above, it is possible to obtain devices implantable in the human body such as catheters, for which it can be useful to have a medicated, a non-medicated, an X-ray visible, a colored, etcetera version.

Alternatively, with the above mentioned material it is possible to obtain some devices implantable in the human body such as some medical "threads", for which it could be useful to have a medicated version, for example comprising a medical substance, such as an antibiotic and/or a radio-opaque substance. Such medical "threads" can be used, for example, for releasing the above mentioned medical substance in soft tissues and they are then unthreaded and extracted from the human body, once their function is accomplished.

In one version of the invention, the biocompatible material is suitable for manufacturing devices implantable in the human body or spacer devices able to absorb such pharmaceutical or medical substances at a later time, after their molding. In fact, such materials—and thus also the resulting devices—are provided with pores or are porous.

The porosity of the device makes it able to absorb, for example by capillarity, such substances after its molding.

In a further version, such devices are made of a material already loaded with at least one pharmaceutical or medical substance but, being porous, once molded they can absorb another substance, the same or different with respect to that already therein contained.

According to a further version, the biocompatible plastic material comprises at least one pharmaceutical or medical substance, is moldable, for example after thermic melting, for manufacturing of a semi-finished product (for example a cylindrical bar, e.g. having dimensions 100×1000 mm). Such semi-finished product can also be further machined or finished, for example by machine-tools or working techniques for chip removal, or suitable knifes or cutters.

Such working methodologies can be kept at a low cutting speed so as to keep a not too high temperature, for example lower than the degradation temperature of the plastic material and/or the pharmaceutical or medical substance, in such a way that heatings or degradations thereof do not occur even during the working steps of the semi-finished product.

In this way it has been seen how the biocompatible material according to the invention, being moldable, allows the manufacturing of devices implantable in the human body or spacer devices, which is fast, easy and in case customizable with regard to both the shape and the dimensions, and also the pharmaceutical or medical substances therein contained, depending on the surgical and anatomical needs of the patient.

The present invention also relates to a device implantable in the human body or spacer device for treating a bone or joint location, comprising a biocompatible and implantable in the human body plastic material according to the present invention.

Such devices, de facto, comprise a pharmaceutical or medical substance (and in case a radio-opacifying agent and/or a further additive), as previously described for the plastic material according to the present invention.

Such devices are manufactured by molding, for example by injection molding or thermo-injection or extrusion or by means of molding presses or a thermoplastic or thermosetting molding technique.

In order to obtain the present invention, one important aspect is that of keeping a melting or softening temperature of the plastic material lower than the degradation temperature of the pharmaceutical or medical substance therein contained, so as to prevent the degradation of the latter during the molding steps of the material thereby obtained.

With the present invention it is possible to obtain directly a device to be implanted in the human body or it is possible to obtain a semi-finished product from which, by means of suitable processing, it is possible to obtain a device to be implanted in the human body.

The invention, as it is conceived, is susceptible of many modifications and variations all falling within the scope of the inventive concept.

The characteristics presented in one version or embodiment can be combined with those of another version or embodiment, without exiting the scope of the present invention.

Moreover, all the details can be substituted by other technically equivalent elements. In practice, the employed materials, as well as the contingent shapes and dimensions, can be any depending on the needs without exiting, for this reason, the scope of protection of the following claims.

The invention claimed is:

1. A material which is antibiotic-loaded, biocompatible and implantable in the human body, for the obtainment of a device that can be implanted in the human body or a spacer device in order to treat a bone or a joint location, wherein said material is a solid-in-solid dispersion comprising:
   a plastic material in the form of granules or powder comprising ultra high molecular weight polyethylene (UHMWPE) or polyethylene (PE) or low density polyethylene or high density polyethylene or a mixture of the above, and
   at least one pharmaceutical or medical substance, in the form of powder or granules and uniformly distributed in the plastic material, comprising:
      at least one antibiotic, wherein said antibiotic is gentamicin sulphate,
      a radio-opacifying agent, and
   a soluble and/or resorbable ceramic material, in form of powder or granules, that is tricalcium phosphate or calcium sulphate or hydroxyapatite, or alumina in its chemical forms, wherein said material is moldable at a temperature lower than 180° C., in order to avoid gentamicin degradation.

2. The material according to claim 1, wherein said plastic material is crushed or granulated or reduced in the form of granules or of powder.

3. The material according to claim 1, wherein said material is a material moldable by means of injection molding or thermo-injection or extrusion or by means of molding presses or using a thermoplastic and/or thermosetting molding technique.

4. The material according to claim 1, wherein said pharmaceutical or medical substance further comprises another antibiotic, or an antiseptic agent of organic or inorganic nature, a bacteriostatic agent that is silver in its forms of metallic powder or salts, citrate, proteinate, colloidal, electrolytic, or other forms that can be used in the human body, or that is copper or gold in their forms, or as salts.

5. The material according to claim 1, wherein said radio-opacifying agent comprises tungsten, tantalum or silver metallic powders or salts, barium sulphate, zirconium oxide, bismuth oxide, and/or wherein said further additive comprises coloring substances of the biocompatible type and adapted to be introduced in the human body.

6. The material according to claim 1, wherein said at least one pharmaceutical or medical substance consists of gentamicin sulphate.

7. A device implantable in the human body or spacer device for treating a bone or a joint location, comprising a biocompatible antibiotic-loaded material and that can be implanted in the human body, wherein said material is a solid-in-solid dispersion comprising:
   a plastic material in the form of granules or powder comprising polyethylene (PE) or ultra high molecular weight polyethylene (UHMWPE) or low density polyethylene or high density polyethylene or a mixture of the above,
   wherein said material comprises at least one pharmaceutical or medical substance in the form of powder or granules and uniformly distributed in the plastic material, comprising:
      at least one antibiotic, wherein said antibiotic is gentamicin sulphate to be eluted in the treatment area during use,
   a radio-opacifying agent,
   a soluble and/or resorbable ceramic material, in form of powder or granules, that is tricalcium phosphate or calcium sulphate or hydroxyapatite, or alumina in its chemical forms, wherein said material is moldable at a temperature lower than 180° C., in order to avoid gentamicin degradation, and wherein said device is porous, and is able, once molded, to absorb another pharmaceutical or medical substance.

8. The device according to claim 7, wherein said device is obtained by means of working of finishing of a semi-finished product obtained by molding of said material by injection or thermo-injection or extrusion or by means of molding presses or using a thermoplastic and/or thermosetting molding technique.

9. The device according to claim 7, wherein said pharmaceutical or medical substance consist of gentamicin sulphate or wherein said pharmaceutical or medical substance further comprises another antibiotic, or an antiseptic agent of organic or inorganic nature, a bacteriostatic agent that is silver in its forms of metallic powder or salts such as citrate, proteinate, colloidal, electrolytic, or other forms that can be used in the human body, or that is copper or gold in their forms or as salts.

10. The device according to claim 7, wherein said radio-opacifying agent comprises tungsten, tantalum or silver metallic powders or salts, barium sulphate, zirconium oxide, bismuth oxide, and/or wherein said further additive comprises a soluble and/or reabsorbable ceramic material, in form of powder or granules, that is tricalcium phosphate or calcium sulphate or hydroxyapatite, or alumina in its chemical forms, or comprises coloring substances of the biocompatible type and adapted to be introduced in the human body.

11. The device according to claim 7, wherein said biocompatible antibiotic-loaded material is porous.

12. A semi-finished product for the realization of a device implantable in the human body or of a spacer device for the treatment of a bone or articular location, comprising the material according to claim 1, wherein said plastic antibiotic-loaded material, after thermic melting, is molded for manufacturing of said semi-finished product.

13. A method for the obtainment of a material biocompatible and implantable in the human body according to claim 1, comprising the following steps:
   providing a plastic material comprising polyethylene (PE) or low density polyethylene or high density polyethylene or ultra high molecular weight polyethylene (UHMWPE) or a mixture of the above,
   wherein said plastic material comprises a crushed or granulated or powdered material,
   providing at least one pharmaceutical or medical substance in the form of powder or granules and uniformly distributed in the plastic material, comprising:
   at least one antibiotic, wherein said antibiotic is gentamicin sulphate to be eluted in the treatment area during use,
   providing a radio-opacifying agent, and
   a soluble and/or resorbable ceramic material, in form of powder or granules, that is tricalcium phosphate or calcium sulphate or hydroxyapatite, or alumina in its chemical forms, or coloring substances of the biocompatible type and adapted to be introduced in the human body,
   obtaining a solid-in-solid dispersion of said plastic material and said at least one pharmaceutical or medical substance uniformly distributed in the plastic material,
   heating said solid-in-solid dispersion up to reaching a threshold temperature, under which said solid-in-solid dispersion melts or softens without being degraded, and
   extruding said melted or softened solid-in-solid dispersion, or
   molding by softening or thermal sintering said melted or softened solid-in-solid dispersion, at a temperature lower than 180° C., in order to avoid gentamicin degradation, in order to obtain a device that can be implanted in the human body or a spacer device for treating a bone or a joint location or a semi-finished product for the further obtainment of a device that can be implanted in the human body or a spacer device for treating a bone or a joint location, wherein said obtained device is porous and is able, once molded, to absorb another pharmaceutical or medical substance that is gentamicin sulphate or different from gentamicin sulphate.

14. The method according to claim 13, comprising a step of inserting said solid-on-solid dispersion in an apparatus, able to melt the materials therein contained at about 130° C.

* * * * *